US010589103B2

(12) United States Patent
Mathur et al.

(10) Patent No.: US 10,589,103 B2
(45) Date of Patent: *Mar. 17, 2020

(54) EXTERNAL PULSE GENERATOR DEVICE AND ASSOCIATED METHODS FOR TRIAL NERVE STIMULATION

(71) Applicant: Axonics Modulation Technologies, Inc., Irvine, CA (US)

(72) Inventors: Prabodh Mathur, Laguna Niguel, CA (US); Rinda Sama, Irvine, CA (US); Dennis Schroeder, Irvine, CA (US); Eric Schmid, Irvine, CA (US); Stuart Karten, Irvine, CA (US)

(73) Assignee: AXONICS MODULATION TECHNOLOGIES, INC., Irvine, CA (US)

( * ) Notice: Subject to any disclaimer, the term of this patent is extended or adjusted under 35 U.S.C. 154(b) by 55 days.

This patent is subject to a terminal disclaimer.

(21) Appl. No.: 15/719,461

(22) Filed: Sep. 28, 2017

(65) Prior Publication Data

US 2018/0117344 A1    May 3, 2018

Related U.S. Application Data

(63) Continuation of application No. 14/827,081, filed on Aug. 14, 2015, now Pat. No. 9,802,051.
(Continued)

(51) Int. Cl.
*A61N 1/37* (2006.01)
*A61N 1/372* (2006.01)
(Continued)

(52) U.S. Cl.
CPC ..... *A61N 1/37241* (2013.01); *A61N 1/36007* (2013.01); *A61N 1/36017* (2013.01);
(Continued)

(58) Field of Classification Search
None
See application file for complete search history.

(56) References Cited

U.S. PATENT DOCUMENTS 3,646,940 A    3/1972   Timm et al.
4,019,518 A    4/1977   Maurer et al.
(Continued)

FOREIGN PATENT DOCUMENTS

CN    102176945 A    9/2011
CN      1745857 A    3/2016
(Continued)

OTHER PUBLICATIONS

Extended European Search Report for EP15831621.6, dated Feb. 8, 2018, 9 pages.
(Continued)

*Primary Examiner* — Ankit D Tejani
(74) *Attorney, Agent, or Firm* — Kilpatrick Townsend & Stockton LLP (57) ABSTRACT

Systems and methods for providing a trial neurostimulation to a patient for assessing suitability of a permanently implanted neurostimulation are provided herein. In one aspect, a trial neurostimulation system includes an EPG patch adhered to a skin surface of a patient and connected to a lead extending through a percutaneous incision to a target tissue location. The EPG may be a modified version of the IPG used in the permanent system, the EPG may be smaller and/or lighter than the corresponding IPG device. The EPG and a lead extension may be sealed to allow improved patient mobility and reduced risk of infection. The EPG may be compatible with wireless systems used to control and monitor the IPG such that operation and control of the EPG is substantially the same in each system to allow seamless conversion to the permanently implanted system.

19 Claims, 9 Drawing Sheets

Related U.S. Application Data (60) Provisional application No. 62/041,611, filed on Aug. 25, 2014, provisional application No. 62/038,131, filed on Aug. 15, 2014.

(51) Int. Cl.
  *A61N 1/36* (2006.01)
  *A61N 1/05* (2006.01)
  *A61N 1/375* (2006.01)

(52) U.S. Cl.
  CPC .......... *A61N 1/0551* (2013.01); *A61N 1/0558* (2013.01); *A61N 1/36107* (2013.01); *A61N 1/36132* (2013.01); *A61N 1/375* (2013.01)

(56) References Cited

U.S. PATENT DOCUMENTS

| | | | |
|---|---|---|---|
| 4,044,774 A | 8/1977 | Corbin et al. |
| 4,340,062 A | 7/1982 | Thompson et al. |
| 4,558,702 A | 12/1985 | Barreras et al. |
| 4,744,371 A | 5/1988 | Harris |
| 5,690,693 A | 11/1997 | Wang et al. |
| 5,702,428 A | 12/1997 | Tippey et al. |
| 5,702,431 A | 12/1997 | Wang et al. |
| 5,735,887 A | 4/1998 | Barreras, Sr. et al. |
| 5,741,316 A | 4/1998 | Chen et al. |
| 5,876,423 A | 3/1999 | Braun |
| 5,974,344 A | 10/1999 | Shoemaker |
| 6,027,456 A | 2/2000 | Feler et al. |
| 6,035,237 A | 3/2000 | Schulman et al. |
| 6,052,624 A | 4/2000 | Mann |
| 6,055,456 A | 4/2000 | Gerber |
| 6,057,513 A | 5/2000 | Ushikoshi et al. |
| 6,067,474 A | 5/2000 | Schulman et al. |
| 6,076,017 A | 6/2000 | Taylor et al. |
| 6,172,556 B1 | 1/2001 | Prentice |
| 6,178,353 B1 | 1/2001 | Griffith et al. |
| 6,191,365 B1 | 2/2001 | Avellanet |
| 6,208,894 B1 | 3/2001 | Schulman et al. |
| 6,212,431 B1 | 4/2001 | Hahn et al. |
| 6,221,513 B1 | 4/2001 | Lasater |
| 6,246,911 B1 | 6/2001 | Seligman |
| 6,249,703 B1 | 6/2001 | Stanton et al. |
| 6,265,789 B1 | 7/2001 | Honda et al. |
| 6,306,100 B1 | 10/2001 | Prass |
| 6,315,721 B2 | 11/2001 | Schulman et al. |
| 6,354,991 B1 | 3/2002 | Gross et al. |
| 6,360,750 B1 | 3/2002 | Gerber et al. |
| 6,393,325 B1 | 5/2002 | Mann et al. |
| 6,438,423 B1 | 8/2002 | Rezai et al. |
| 6,442,434 B1 | 8/2002 | Zarinetchi et al. |
| 6,466,817 B1 | 10/2002 | Kaula et al. |
| 6,505,075 B1 | 1/2003 | Weiner |
| 6,516,227 B1 | 2/2003 | Meadows et al. |
| 6,584,355 B2 | 6/2003 | Slessman |
| 6,600,954 B2 | 7/2003 | Cohen et al. |
| 6,609,031 B1 | 8/2003 | Law et al. |
| 6,609,032 B1 | 8/2003 | Woods et al. |
| 6,652,449 B1 | 11/2003 | Gross et al. |
| 6,662,051 B1 | 12/2003 | Eraker et al. |
| 6,721,603 B2 | 4/2004 | Zabara et al. |
| 6,735,474 B1 | 5/2004 | Loeb et al. |
| 6,745,077 B1 | 6/2004 | Griffith et al. |
| 6,809,701 B2 | 10/2004 | Amundson et al. |
| 6,836,684 B1 | 12/2004 | Rijkhoff et al. |
| 6,847,849 B2 | 1/2005 | Mamo et al. |
| 6,892,098 B2 | 5/2005 | Ayal et al. |
| 6,895,280 B2 | 5/2005 | Meadows et al. |
| 6,896,651 B2 | 5/2005 | Gross et al. |
| 6,901,287 B2 | 5/2005 | Davis et al. |
| 6,941,171 B2 | 9/2005 | Mann et al. |
| 6,971,393 B1 | 12/2005 | Mamo et al. |
| 6,989,200 B2 | 1/2006 | Byers et al. |
| 6,990,376 B2 | 1/2006 | Tanagho et al. |
| 6,999,819 B2 | 2/2006 | Swoyer et al. |
| 7,051,419 B2 | 5/2006 | Schrom et al. |
| 7,054,689 B1 | 5/2006 | Whitehurst et al. |
| 7,069,081 B2 | 6/2006 | Biggs et al. |
| 7,127,298 B1 | 10/2006 | He et al. |
| 7,142,925 B1 | 11/2006 | Bhadra et al. |
| 7,146,219 B2 | 12/2006 | Sieracki et al. |
| 7,151,914 B2 | 12/2006 | Brewer |
| 7,167,749 B2 | 1/2007 | Biggs et al. |
| 7,177,690 B2 | 2/2007 | Woods et al. |
| 7,177,698 B2 | 2/2007 | Klosterman et al. |
| 7,181,286 B2 | 2/2007 | Sieracki et al. |
| 7,187,978 B2 | 3/2007 | Malek et al. |
| 7,191,005 B2 | 3/2007 | Slessman |
| 7,212,110 B1 | 5/2007 | Martin et al. |
| 7,225,032 B2 | 5/2007 | Schmeling et al. |
| 7,231,254 B2 | 6/2007 | Dilorenzo |
| 7,234,853 B2 | 6/2007 | Givoletti |
| 7,245,972 B2 | 7/2007 | Davis |
| 7,286,880 B2 | 10/2007 | Olson et al. |
| 7,305,268 B2 | 12/2007 | Gliner et al. |
| 7,317,948 B1 | 1/2008 | King et al. |
| 7,324,852 B2 | 1/2008 | Barolat et al. |
| 7,324,853 B2 | 1/2008 | Ayal et al. |
| 7,328,068 B2 | 2/2008 | Spinelli et al. |
| 7,330,764 B2 | 2/2008 | Swoyer et al. |
| 7,359,751 B1 | 4/2008 | Erickson et al. |
| 7,369,894 B2 | 5/2008 | Gerber |
| 7,386,348 B2 | 6/2008 | North et al. |
| 7,387,603 B2 | 6/2008 | Gross et al. |
| 7,396,265 B2 | 7/2008 | Darley et al. |
| 7,415,308 B2 | 8/2008 | Gerber et al. |
| 7,444,181 B2 | 10/2008 | Shi et al. |
| 7,450,991 B2 | 11/2008 | Smith et al. |
| 7,460,911 B2 | 12/2008 | Cosendai et al. |
| 7,463,928 B2 | 12/2008 | Lee et al. |
| 7,470,236 B1 | 12/2008 | Kelleher et al. |
| 7,483,752 B2 | 1/2009 | Von Arx et al. |
| 7,496,404 B2 | 2/2009 | Meadows et al. |
| 7,515,967 B2 | 4/2009 | Phillips et al. |
| 7,532,936 B2 | 5/2009 | Erickson et al. |
| 7,539,538 B2 | 5/2009 | Parramon et al. |
| 7,551,960 B2 | 6/2009 | Forsbera et al. |
| 7,555,346 B1 | 6/2009 | Woods et al. |
| 7,565,203 B2 | 7/2009 | Greenberg et al. |
| 7,578,819 B2 | 8/2009 | Bleich et al. |
| 7,580,752 B2 | 8/2009 | Gerber et al. |
| 7,582,053 B2 | 9/2009 | Gross et al. |
| 7,617,002 B2 | 11/2009 | Goetz |
| 7,640,059 B2 | 12/2009 | Forsberg et al. |
| 7,643,880 B2 | 1/2010 | Tanagho et al. |
| 7,706,889 B2 | 4/2010 | Gerber et al. |
| 7,720,547 B2 | 5/2010 | Denker et al. |
| 7,725,191 B2 | 5/2010 | Greenberg et al. |
| 7,734,355 B2 | 6/2010 | Cohen et al. |
| 7,738,963 B2 | 6/2010 | Hickman et al. |
| 7,738,965 B2 | 6/2010 | Phillips et al. |
| 7,747,330 B2 | 6/2010 | Nolan et al. |
| 7,771,838 B1 | 8/2010 | He et al. |
| 7,774,069 B2 | 8/2010 | Olson et al. |
| 7,801,619 B2 | 9/2010 | Gerber et al. |
| 7,813,803 B2 | 10/2010 | Heruth et al. |
| 7,813,809 B2 | 10/2010 | Strother et al. |
| 7,826,901 B2 | 11/2010 | Lee et al. |
| 7,848,818 B2 | 12/2010 | Barolat et al. |
| 7,904,167 B2 | 3/2011 | Klosterman et al. |
| 7,912,555 B2 | 3/2011 | Swoyer et al. |
| 7,925,357 B2 | 4/2011 | Phillips et al. |
| 7,932,696 B2 | 4/2011 | Peterson |
| 7,933,656 B2 | 4/2011 | Sieracki et al. |
| 7,935,051 B2 | 5/2011 | Miles et al. |
| 7,937,158 B2 | 5/2011 | Erickson et al. |
| 7,952,349 B2 | 5/2011 | Huang et al. |
| 7,957,818 B2 | 6/2011 | Swoyer |
| 7,979,119 B2 | 7/2011 | Kothandaraman et al. |
| 7,979,126 B2 | 7/2011 | Payne et al. |
| 7,988,507 B2 | 8/2011 | Darley et al. |
| 8,000,782 B2 | 8/2011 | Gharib et al. |
| 8,000,805 B2 | 8/2011 | Swoyer et al. |

(56) References Cited

U.S. PATENT DOCUMENTS

| | | |
|---|---|---|
| 8,005,535 B2 | 8/2011 | Gharib et al. |
| 8,005,549 B2 | 8/2011 | Boser et al. |
| 8,005,550 B2 | 8/2011 | Boser et al. |
| 8,019,423 B2 | 9/2011 | Possover |
| 8,024,047 B2 | 9/2011 | Olson et al. |
| 8,036,756 B2 | 10/2011 | Swoyer et al. |
| 8,044,635 B2 | 10/2011 | Peterson |
| 8,050,769 B2 | 11/2011 | Gharib et al. |
| 8,055,337 B2 | 11/2011 | Moffitt et al. |
| 8,068,912 B2 | 11/2011 | Kaula et al. |
| 8,083,663 B2 | 12/2011 | Gross et al. |
| 8,103,360 B2 | 1/2012 | Foster |
| 8,116,862 B2 | 2/2012 | Stevenson et al. |
| 8,121,701 B2 | 2/2012 | Woods et al. |
| 8,129,942 B2 | 3/2012 | Park et al. |
| 8,131,358 B2 | 3/2012 | Moffitt et al. |
| 8,140,168 B2 | 3/2012 | Olson et al. |
| 8,145,324 B1 | 3/2012 | Stevenson et al. |
| 8,150,530 B2 | 4/2012 | Wesselink |
| 8,175,717 B2 | 5/2012 | Haller et al. |
| 8,180,451 B2 | 5/2012 | Hickman et al. |
| 8,180,452 B2 | 5/2012 | Shaquer |
| 8,180,461 B2 | 5/2012 | Mamo et al. |
| 8,214,042 B2 | 7/2012 | Ozawa et al. |
| 8,214,048 B1 | 7/2012 | Whitehurst et al. |
| 8,214,051 B2 | 7/2012 | Sieracki et al. |
| 8,219,196 B2 | 7/2012 | Torgerson |
| 8,219,202 B2 | 7/2012 | Giftakis et al. |
| 8,233,990 B2 | 7/2012 | Goetz |
| 8,255,057 B2 | 8/2012 | Fang et al. |
| 8,311,636 B2 | 11/2012 | Gerber et al. |
| 8,314,594 B2 | 11/2012 | Scott et al. |
| 8,332,040 B1 | 12/2012 | Winstrom |
| 8,340,786 B2 | 12/2012 | Gross et al. |
| 8,362,742 B2 | 1/2013 | Kallmyer |
| 8,369,943 B2 | 2/2013 | Shuros et al. |
| 8,382,059 B2 | 2/2013 | Le Gette et al. |
| 8,386,048 B2 | 2/2013 | McClure et al. |
| 8,417,346 B2 | 4/2013 | Giftakis et al. |
| 8,423,146 B2 | 4/2013 | Giftakis et al. |
| 8,447,402 B1 | 5/2013 | Jiang et al. |
| 8,447,408 B2 | 5/2013 | North et al. |
| 8,452,409 B2 | 5/2013 | Bachinski et al. |
| 8,457,756 B2 | 6/2013 | Rahman |
| 8,457,758 B2 | 6/2013 | Olson et al. |
| 8,480,437 B2 | 7/2013 | Dilmaghanian et al. |
| 8,494,625 B2 | 7/2013 | Hargrove |
| 8,515,545 B2 | 8/2013 | Trier |
| 8,538,530 B1 | 9/2013 | Orinski |
| 8,543,223 B2 | 9/2013 | Sage et al. |
| 8,549,015 B2 | 10/2013 | Barolat |
| 8,554,322 B2 | 10/2013 | Olson et al. |
| 8,555,894 B2 | 10/2013 | Schulman et al. |
| 8,562,539 B2 | 10/2013 | Marino |
| 8,571,677 B2 | 10/2013 | Torgerson et al. |
| 8,577,474 B2 | 11/2013 | Rahman et al. |
| 8,588,917 B2 | 11/2013 | Whitehurst et al. |
| 8,626,314 B2 | 1/2014 | Swoyer et al. |
| 8,644,933 B2 | 2/2014 | Ozawa et al. |
| 8,655,451 B2 | 2/2014 | Klosterman et al. |
| 8,700,175 B2 | 4/2014 | Fell |
| 8,700,177 B2 | 4/2014 | Strother et al. |
| 8,725,269 B2 | 5/2014 | Nolan et al. |
| 8,738,138 B2 | 5/2014 | Fundeburk et al. |
| 8,738,141 B2 | 5/2014 | Smith et al. |
| 8,738,148 B2 | 5/2014 | Olson et al. |
| 8,750,985 B2 | 6/2014 | Parramon et al. |
| 8,761,897 B2 | 6/2014 | Kaula et al. |
| 8,768,452 B2 | 7/2014 | Gerber |
| 8,774,912 B2 | 7/2014 | Gerber |
| 8,892,217 B2 | 11/2014 | Camps et al. |
| 8,954,148 B2 | 2/2015 | Labbe et al. |
| 8,989,861 B2 | 3/2015 | Su et al. |
| 9,089,712 B2 | 7/2015 | Joshi et al. |
| 9,108,063 B2 | 8/2015 | Olson et al. |
| 9,802,051 B2 | 10/2017 | Mathur et al. |
| 2003/0120323 A1 | 6/2003 | Meadows et al. |
| 2005/0104577 A1 | 5/2005 | Matei et al. |
| 2006/0041283 A1 | 2/2006 | Gelfand et al. |
| 2006/0142822 A1 | 6/2006 | Tulgar |
| 2006/0206166 A1 | 9/2006 | Weiner |
| 2007/0060980 A1 | 3/2007 | Strother et al. |
| 2007/0265675 A1 | 11/2007 | Lund et al. |
| 2007/0293914 A1 | 12/2007 | Woods et al. |
| 2008/0161874 A1 | 7/2008 | Bennett et al. |
| 2008/0183236 A1 | 7/2008 | Gerber |
| 2010/0036445 A1 | 2/2010 | Sakai et al. |
| 2010/0076254 A1 | 3/2010 | Jimenez et al. |
| 2010/0076534 A1 | 3/2010 | Mock |
| 2011/0125214 A1 | 5/2011 | Goetz et al. |
| 2011/0152987 A1 | 6/2011 | Wahlgren et al. |
| 2011/0251662 A1 | 10/2011 | Griswold et al. |
| 2011/0282416 A1 | 11/2011 | Hamann et al. |
| 2011/0301667 A1 | 12/2011 | Olson et al. |
| 2012/0041512 A1 | 2/2012 | Weiner |
| 2012/0046712 A1 | 2/2012 | Woods et al. |
| 2012/0130448 A1 | 5/2012 | Woods et al. |
| 2012/0276854 A1 | 11/2012 | Joshi et al. |
| 2012/0276856 A1 | 11/2012 | Joshi et al. |
| 2012/0290055 A1 | 11/2012 | Boggs |
| 2013/0004925 A1 | 1/2013 | Labbe et al. |
| 2013/0006325 A1 | 1/2013 | Woods et al. |
| 2013/0006330 A1 | 1/2013 | Wilder et al. |
| 2013/0006331 A1 | 1/2013 | Weisgarber et al. |
| 2013/0096641 A1 | 4/2013 | Strother et al. |
| 2013/0150925 A1 | 6/2013 | Vamos et al. |
| 2013/0172956 A1 | 7/2013 | Goddard et al. |
| 2013/0197608 A1 | 8/2013 | Eiger |
| 2013/0207863 A1 | 8/2013 | Joshi |
| 2013/0310894 A1 | 11/2013 | Trier |
| 2013/0325097 A1 | 12/2013 | Loest |
| 2013/0331909 A1 | 12/2013 | Gerber |
| 2014/0194948 A1 | 7/2014 | Strother et al. |
| 2014/0222112 A1 | 8/2014 | Fell |
| 2014/0237806 A1 | 8/2014 | Smith et al. |
| 2014/0277270 A1 | 9/2014 | Parramon et al. |
| 2015/0028798 A1 | 1/2015 | Dearden et al. |
| 2015/0088227 A1 | 3/2015 | Shishilla |
| 2015/0094790 A1 | 4/2015 | Shishilla |
| 2015/0100106 A1 | 4/2015 | Shishilla |
| 2015/0214604 A1 | 7/2015 | Zhao et al. |
| 2015/0231402 A1 | 8/2015 | Aghassian |
| 2016/0045745 A1 | 2/2016 | Mathur et al. |

FOREIGN PATENT DOCUMENTS

| | | |
|---|---|---|
| EP | 1680182 A1 | 7/2006 |
| EP | 1680182 B1 | 7/2006 |
| EP | 2243509 A1 | 10/2010 |
| JP | 2011-529718 A | 12/2011 |
| WO | 00/56677 A1 | 3/2000 |
| WO | 2008/021524 A2 | 2/2008 |
| WO | 2011/1059565 A1 | 5/2011 |
| WO | 2013/162709 A1 | 10/2013 |
| WO | 2014/087337 | 6/2014 |
| WO | 2014/087337 A1 | 6/2014 |
| WO | 2014-151160 A1 | 9/2014 |

OTHER PUBLICATIONS

Bosch, J., et al., Sacral (S3) Segmental Nerve Stimulation as a Treatment for Urge Incontinence in Patients With Detrusor Instability: Results of Chronic Electrical Stimulation Using an Implantable Neural Prosthesis, The Journal of Urology, Aug. 1995, vol. 154, pp. 504-507.

Ghovanloo, M., et al., A Small Size Large Voltage Compliance Programmable Current Source for Biomedical Implantable Microstimulators, Proceedings of the 25th Annual International Conference of the IEEE EMBS, Sep. 17-21, 2003, pp. 1979-1982.

Tanagho, E., et al., Bladder Pacemaker: Scientific Basis and Clinical Future, Urology, Dec. 1982, vol. 20, No. 6, pp. 614-619.

U.S. Appl. No. 14/827,074, filed Aug. 14, 2015.

(56) References Cited

OTHER PUBLICATIONS

U.S. Appl. No. 14/991,649, filed Jan. 8, 2016.
U.S. Appl. No. 14/827,108, filed Aug. 14, 2015.
U.S. Appl. No. 14/991,752, filed Jan. 8, 2016.
U.S. Appl. No. 14/827,095, filed Aug. 14, 2015.
U.S. Appl. No. 14/827,067, filed Aug. 14, 2015.
U.S. Appl. No. 14/991,784, filed Jan. 8, 2016.
U.S. Appl. No. 62/101,888, filed Jan. 9, 2015.
U.S. Appl. No. 62/101,899, filed Jan. 9, 2015.
U.S. Appl. No. 62/101,897, filed Jan. 9, 2015.
U.S. Appl. No. 62/110,274, filed Jan. 30, 2015.
U.S. Appl. No. 62/038,122, filed Aug. 15, 2014.
U.S. Appl. No. 62/101,666, filed Jan. 9, 2015.
U.S. Appl. No. 62/101,884, filed Jan. 9, 2015.
U.S. Appl. No. 62/101,782, filed Jan. 9, 2015.
U.S. Appl. No. 62/191,134, filed Jul. 10, 2015.

EXTERNAL PULSE GENERATOR DEVICE AND ASSOCIATED METHODS FOR TRIAL NERVE STIMULATION

CROSS-REFERENCES TO RELATED APPLICATIONS

The present application is a continuation of U.S. Non-Provisional application Ser. No. 14/827,081 filed on Aug. 14, 2015, which claims the benefit of priority of U.S. Provisional Application No. 62/038,131 filed on Aug. 15, 2014; and 62/041,611 filed Aug. 25, 2014; the entire contents of which are incorporated herein by reference.

The present application is related to concurrently filed U.S. Non-Provisional Patent application Ser. No. 14/827,074, entitled "Devices and Methods for Anchoring of Neurostimulation Leads"; Ser. No. 14/827,108, entitled "Electromyographic Lead Positioning and Stimulation Titration in a Nerve Stimulation System for Treatment of Overactive Bladder;" Ser. No. 14/827,095, entitled "Integrated Electromyographic Clinician Programmer For Use With an Implantable Neurostimulator'"; and Ser. No. 14/827,067, entitled "Systems and Methods for Neurostimulation Electrode Configurations Based on Neural Localization"; and U.S. Provisional Application Nos. 62/101,666, entitled "Patient Remote and Associated Methods of Use With a Nerve Stimulation System" filed on Jan. 9, 2015; 62/101,884, entitled "Attachment Devices and Associated Methods of Use With a Nerve Stimulation Charging Device" filed on Jan. 9, 2015; 62/101,782, entitled "Improved Antenna and Methods of Use For an Implantable Nerve Stimulator" filed on Jan. 9, 2015; and 62/191,134, entitled "Implantable Nerve Stimulator Having Internal Electronics Without ASIC and Methods of Use" filed on Jul. 10, 2015; each of which is assigned to the same assignee and incorporated herein by reference in its entirety for all purposes.

BACKGROUND OF THE INVENTION

Treatments with implanted neurostimulation systems have become increasingly more common in recent years. While such systems have shown promise in treating a number of chronic conditions, effectiveness of treatment may vary considerably between patients and viability of treatment can be difficult to determine before implantation. Although conventional methods of implantation often utilize preliminary testing with a temporary, partly implanted neurostimulation systems to assess viability of treatment, such systems may not provide an accurate representation of treatment with a fully implanted device. In addition, such systems are often bulky, uncomfortable and limit patient mobility, such that many patients elect not to receive a temporary system or a fully implanted system. In addition, many such temporary partly implanted systems may not operate in the same manner as their fully implanted counterparts due to differences between pulse generators or changes in position of the neurostimulation leads during conversion. Therefore, it is desirable to provide methods and devices for providing trial treatment systems that provide a more accurate representation of treatment, improve patient comfort and provide consistent treatment outcomes as compared to fully implanted neurostimulation systems.

BRIEF SUMMARY OF THE INVENTION

The present invention relates to neurostimulation treatment systems, and in particular a neurostimulation treatment having a partly implanted neurostimulation lead extending to an external pulse generator for conducting a trial neurostimulation treatment for assessing viability of a fully implanted system. In one aspect, the system includes a partly implanted neurostimulation lead that extends from one or more implanted neurostimulation electrodes to an external pulse generator (EPG) supported in an adherent patch affixed to the patient's skin. In certain embodiments, the EPG is sealed within a laminated flexible patch adhered to the patient so as to allow the patient to partake in normal everyday activities, including showering. The adherent patch may utilize a skin-compatible adhesive of sufficient strength to maintain adherence for the duration of the trial period. In some aspects, the trial period may be as little as 4-7 days, while in other aspects the trial period may extend two weeks or more, typically about four weeks. The system may further use additional adherent patches to seal the percutaneous incision through which the partly implanted lead extends and to maintain a position of the lead extending outside the body and prevent migration of the percutaneous portion of the lead. This is advantageous since often, during the trial period, the anchor portion of the lead may not be deployed so as to allow adjustment of the neurostimulation electrodes during the trial period.

In one aspect, a neurostimulation system includes an implantable neurostimulation lead having one or more conductors disposed within a lead body, the one or more conductors extending from a proximal end of the lead to one or more neurostimulation electrodes disposed at or near a distal end of the lead; an EPG electrically coupleable to the implantable lead, the pulse generator being electrically coupled with the one or more neurostimulation electrodes when electrically coupled with the implantable lead, wherein the pulse generator is configured to generate a plurality of electrical impulses for delivering a neurostimulation treatment to a patient through the one or more neurostimulation electrodes when implanted at a target location; and an adherent patch adapted to substantially cover the EPG and adhere to a skin of the patient so as to support the EPG on the skin of the patient for a duration of a trial period to assess efficacy of the neurostimulation treatment. The adherent patch comprises a flexible laminated patch, wherein the EPG is sealed within the laminated patch so as to be water resistant. The adherent patch includes a skin-compatible adhesive and material so as to be suitable for continuous adherence to the patient skin for the duration of the trial period, which can be anywhere from 4 days to 4 weeks or more.

In another aspect, the system may include a neurostimulation lead extension connected at one end to the proximal end of the implantable neurostimulation lead and coupleable with the EPG. The implantable neurostimulation lead is of a length suitable for implantation within a fully implanted neurostimulation system without removal of the distal portion from the target location after the trial period, wherein in the fully implanted neurostimulation system, the implantable pulse generator is implanted in a lower back region. The lead extension may of sufficient length to position the EPG patch in a desired location, such a patient's abdomen. In one aspect, the lead extension may be coupled to the proximal end of the lead by a connector. The connector may operate in a similar manner as the interface on the IPG such that the lead can be disconnected from the lead extension and directly connected to the IPG during conversion to a permanent system.

In certain aspects, the EPG is a modified version of the IPG such that they operate in a similar manner in delivering electrical pulses to the neurostimulation pulses. The EPG is typically smaller and/or lighter than the implantable pulse generator such as by removing certain components of the IPG, such as replacing wireless charging coils and associated components of the IPG with a battery, or utilizing lighter, thinner housing materials such that the EPG is disposable. The EPG may be configured to be compatible with external control devices used with the IPG to allow easy transition between the devices during conversion to a permanently implanted system.

In another aspect, a neurostimulation system in accordance with aspect of the invention includes an implantable lead having one or more conductors disposed within a lead body, the one or more conductors extending from a proximal end of the lead to one or more neurostimulation electrodes disposed at or near a distal end of the lead; an EPG coupled to the proximal end of the implantable lead and sealed within an adherent patch attached to the patient, typically in a lower abdominal region. The EPG is configured to generate a plurality of electrical impulses to the implantable lead, the pulse generator being configured to generate a plurality of electrical impulses for delivering a neurostimulation treatment to a patient through the one or more neurostimulation electrodes when implanted at a target location; and an anchor coupled with the lead body just proximal of the electrodes.

In one aspect, the invention includes an anchoring body having a plurality of tines disposed along the anchoring body. The plurality of tines are biased toward a deployed position in which the tines extend laterally outward from the anchor body so as to engage tissue sufficiently to inhibit axial displacement of the implanted lead. The tines are constructed so as to be resiliently deflectable toward the helical body during implantation so as to fold inward toward the helical anchoring body when constrained by a delivery sheath to facilitate delivery to the target location during implantation. Typically, during the trial period, the sheath is disposed over the plurality of tines and the position of the neurostimulation lead is maintained by the additional adherent patches covering the portion of the lead extending outside the body to the EPG patch. This allows the lead position to be altered as needed during the trial to determine the most suitable lead position for treatment. If the trial proves successful, then the outer sheath can be withdrawn and the tines deployed so as to anchor the lead in position, after which the lead can be fully implanted along with an IPG. Methods of providing a trial treatment with such devices are also provided herein.

Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

DETAILED DESCRIPTION OF THE INVENTION

Neurostimulation has been used for many years to treat a variety of conditions, from chronic pain, to erectile dysfunction and various urinary dysfunctions. While neurostimulation has proven effective in many applications, effective therapy often relies on consistently delivering therapeutic activation by one or more neurostimulation electrodes to particular nerves or targeted regions with a pulse generator. In recent years, fully implantable neurostimulation have become increasingly more commonplace. Although such implantable systems provide patients with greater freedom and mobility, the neurostimulation electrodes of such systems are more difficult to adjust once they are implanted. The neurostimulation electrodes are typically provided on a distal end of an implantable lead that is advanced through a tunnel formed in a patient tissue.

Figure 1:
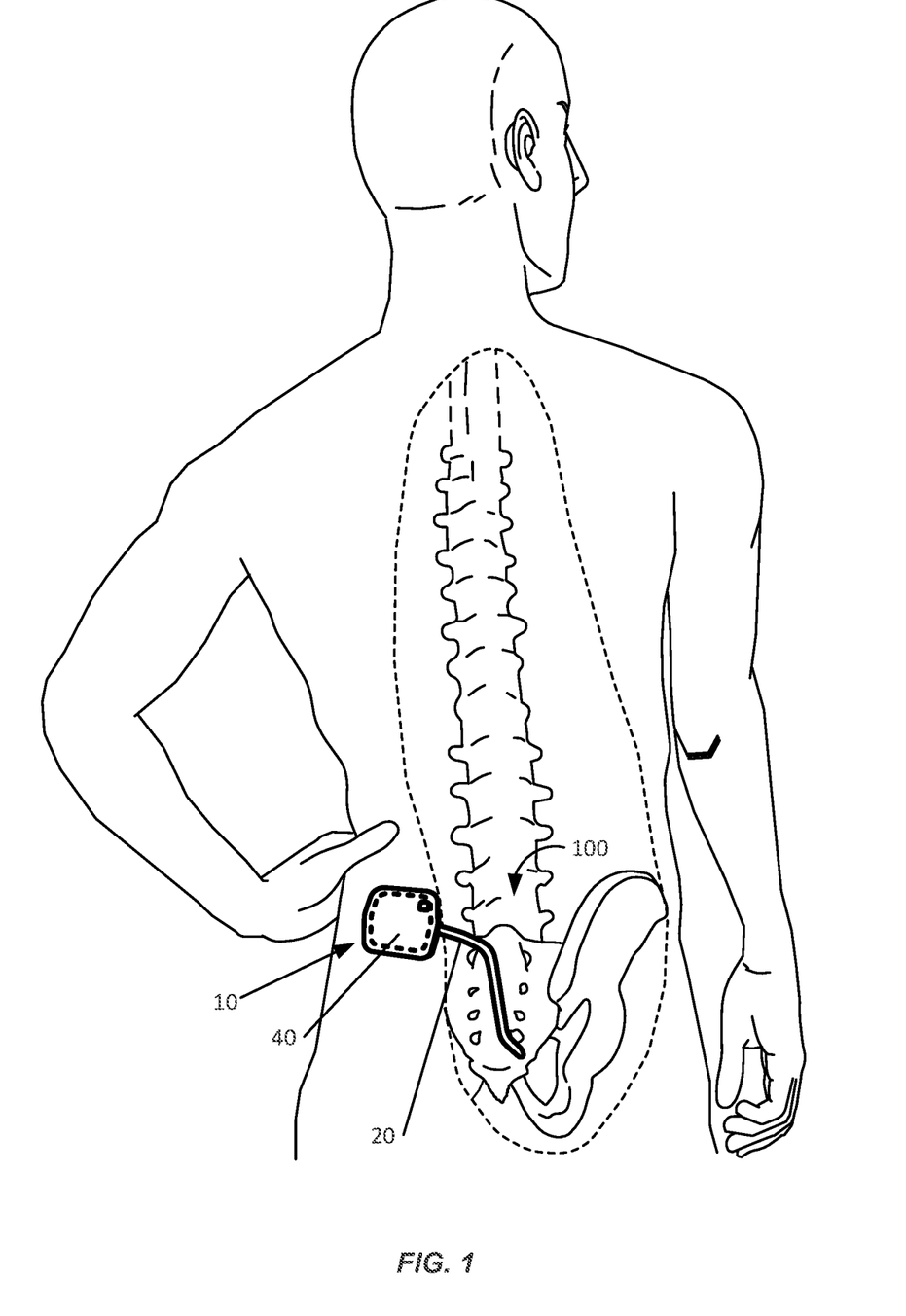
FIG. 1 is a schematic illustration of a trial neurostimulation system having a partly implanted lead extending to an EPG patch adhered to the skin of the patient, in accordance with aspects of the invention.

FIG. 1 schematically illustrates a use of a trial neurostimulation system utilizing an EPG patch, in accordance with aspect of the invention. Such a trial neurostimulation system can be used to assess viability of a fully implantable neurostimulation system. Implantable neurostimulation systems can be used in treating patients with, for example, chronic, severe, refractory neuropathic pain originating from peripheral nerves or various urinary and bowel dysfunctions. Implantable neurostimulation systems can be used to either stimulate a target peripheral nerve or the posterior epidural space of the spine. An implantable neurostimulation system includes an implanted pulse generator, typically implanted in a lower back region. In some embodiments, the pulse generator can generate one or more non-ablative electrical pulses that are delivered to a nerve to control pain or cause some other desired effect. In some applications, the pulses having a pulse amplitude of between 0-1,000 mA, 0-100 mA, 0-50 mA, 0-25 mA, and/or any other or intermediate range of amplitudes may be used. One or more of the pulse generators can include a processor and/or memory adapted to provide instructions to and receive information from the other components of the implantable neurostimulation system. The processor can include a microprocessor, such as a microprocessor from Intel® or Advanced Micro Devices, Inc.®, or the like. An implantable pulse generator may implement an energy storage feature, such as one or more capacitors or a battery, and typically includes a wireless charging unit.

The electrical pulses generated by the pulse generator are delivered to one or more nerves and/or to a target location via one or more leads that include one or more neurostimulation electrodes at or near the distal end. The leads can have a variety of shapes, can be a variety of sizes, and can be made from a variety of materials, which size, shape, and materials can be dictated by the application or other factors. In some applications, the leads may be implanted to extend along the spine or through one of the foramen of the sacrum, such as shown in FIG. 1, such as in sacral nerve stimulation. In other applications, the leads may be implanted in a peripheral portion of the patient's body, such as in the arms or legs, and can be configured to deliver one or more electrical pulses to the peripheral nerve such as may be used to relieve chronic pain.

One or more properties of the electrical pulses can be controlled via a controller of the implanted pulse generator. In some embodiments, these properties can include, for example, the frequency, strength, pattern, duration, or other aspects of the timing and magnitude of the electrical pulses. These properties can include, for example, a voltage, a current, or the like. This control of the electrical pulses can include the creation of one or more electrical pulse programs, plans, or patterns, and in some embodiments, this can include the selection of one or more pre-existing electrical pulse programs, plans, or patterns. In the embodiment depicted in FIG. 1, the implantable neurostimulation system 100 includes a controller in the implantable pulse generator having one or more pulse programs, plans, or patterns and/or to select one or more of the created pulse programs, plans, or patterns.

Sacral nerve neuromodulation (SNM), also known as sacral nerve stimulation (SNS), is defined as the implantation of a permanent device that modulates the neural pathways controlling bladder or rectal function. This policy addresses use of SNM in the treatment of urinary or fecal incontinence, urinary or fecal nonobstructive retention, or chronic pelvic pain in patients with intact neural innervation of the bladder and/or rectum.

Treatment using SNM, also known as SNS, is one of several alternative modalities for patients with fecal or urinary incontinence (urge incontinence, significant symptoms of urgency-frequency, or nonobstructive urinary retention) who have failed behavioral (e.g., prompted voiding) and/or pharmacologic therapies. Urge incontinence is defined as leakage of urine when there is a strong urge to void. Urgency-frequency is an uncontrollable urge to urinate, resulting in very frequent, small volumes and is a prominent symptom of interstitial cystitis (also called bladder pain syndrome). Urinary retention is the inability to completely empty the bladder of urine. Fecal incontinence can result from a variety of mechanisms, including rectal wall compliance, neural pathways, nervous system, and voluntary and involuntary muscles. Incontinence is more common in women, often associated with muscular and neural damage that may occur during vaginal child delivery.

The SNM device consists of an implantable pulse generator that delivers controlled electrical impulses. This pulse generator is attached to wire leads that connect to the sacral nerves, most commonly the S3 nerve root. Two external components of the system help control the electrical stimulation. A patient remote control is kept by the patient and can be used to turn the device on or off or to adjust stimulation intensity. A console programmer is kept by the physician and used to adjust the settings of the pulse generator.

In a conventional approach, prior to implantation of the permanent device, patients undergo an initial testing phase to estimate potential response to treatment. The first type of testing developed was percutaneous nerve evaluation (PNE). This procedure is done under local anesthesia, using a test needle to identify the appropriate sacral nerve(s). Once identified, a temporary wire lead is inserted through the test needle and left in place for 4 to 7 days. This lead is connected to an external stimulator, which is carried by patients in their pocket or on their belt. The results of this test phase are used to determine whether patients are appropriate candidates for the permanent device. For example, for overactive bladder, if patients show a 50 percent or greater reduction in symptom frequency, they are deemed eligible for the permanent device.

The second type of testing is a 2-stage surgical procedure. In Stage 1, a quadripolar-tined lead is implanted (stage 1). The testing phase can last as long as several weeks, and if patients show a specified reduction in symptom frequency, they can proceed to Stage 2 of the surgery, which is permanent implantation of the neuromodulation device. The 2-stage surgical procedure has been used in various ways. These include its use instead of PNE, for patients who failed PNE, for patients with an inconclusive PNE, or for patients who had a successful PNE to further refine patient selection.

The permanent device is implanted under local or general anesthesia. An incision is made over the lower back and the electrical leads are placed in contact with the sacral nerve root(s). The wire leads are extended underneath the skin to a pocket incision where the pulse generator is inserted and connected to the wire leads. Following implantation, the physician programs the pulse generator to the optimal settings for that patient.

In the instance of bladder dysfunction, a trial period of sacral nerve neuromodulation with either percutaneous nerve stimulation or a temporarily implanted lead may be considered medically necessary (at least for purposed of insurance coverage) in patients that meet all of the following criteria: (1) a diagnosis of at least one of the following: urge incontinence; urgency-frequency syndrome; non-obstructive urinary retention; and overactive bladder; (2) there is documented failure or intolerance to at least two conventional therapies (e.g., behavioral training such as bladder training, prompted voiding, or pelvic muscle exercise training, pharmacologic treatment for at least a sufficient duration to fully assess its efficacy, and/or surgical corrective therapy); (3) the patient is an appropriate surgical candidate; and (4) incontinence is not related to a neurologic condition.

Permanent implantation of a sacral nerve neuromodulation device may be considered medically necessary in patients who meet all of the following criteria: (1) all of the criteria (1) through (4) in the previous paragraph are met; and (2) trial stimulation period demonstrates at least 50% improvement in symptoms over a period of at least one week.

Other urinary/voiding applications of sacral nerve neuromodulation are considered investigational, including but not limited to treatment of stress incontinence or urge incontinence due to a neurologic condition, e.g., detrusor hyperreflexia, multiple sclerosis, spinal cord injury, or other types of chronic voiding dysfunction. (See policy description of sacral nerve neuromodulation/stimulation coverage provided by Blue Cross Blue Shield available online at: http://www.bcbsms.com/com/bcbsms/apps/PolicySearch/views/ViewPolicy.php?&noprint=yes&path=%2Fpolicy%2Femed%2FSacral_Nerve_Stimulation.html)

Studies have shown that trial conversion rates, which is the rate at which patients convert a trial system to a permanently implanted system, are higher for Stage 1 trials than for PNE. For example, one study found that PNE trials resulted in a trial conversion rate of 40-50%, while Stage 1 trials resulted in 70-90% conversion, suggesting that Stage 1 generally provides a better indication of effectiveness of treatments. (See 1 Baster and Kim (2010). *Curr urol Rep*).

In another conventional approach, a similar method is used in peripheral neurostimulation (PNS) treatment systems. Generally, candidates for peripheral neurostimulation are assessed to determine their suitability for undergoing the PNS procedure. Prior to the surgery, the patient will undergo pre-surgical testing that includes routine blood tests as well as neuropsychological evaluation. The PNS procedure itself is typically performed in two separate stages. Each stage takes about one hour, and the patient can go home the same day.

In this aspect, Stage 1 involves implanting of trial electrodes, via small needles, which are connected to an external pulse generator (EPG), typically worn on a belt of the patient. A number of stimulation programs are administered over the next few days. If this trial demonstrates a significant improvement in the patient's headache or facial pain, permanent implantation can take place. In Stage 2, a new set of electrodes, the width of angel-hair pasta, are implanted under the skin. These are connected to a smaller implantable pulse generator implanted under the skin in the chest, abdomen, or back.

Among the drawbacks associated with these conventional approaches, is the discomfort associated with wearing an EPG, the risk of infection, as well as the additional procedures associated with removal of the implanted test leads and implantable of the permanent leads in Stage 2. In addition, often the EPG provided is different than the IPG that is eventually implanted. Given that efficacy of treatment often relies on precise placement of the neurostimulation electrodes at target tissue locations and consistent, repeatable delivery of neurostimulation therapy with the devices, the effectiveness of a trial period such as in PNE and Stage 1 trial periods are not always indicative of effective treatment with a permanent implanted system. In one aspect, since effectiveness of treatment in a trial period may rely, in part, on a patient's subjective experience, it is desirable if the discomfort and inconvenience of wearing an EPG by the patient can be minimized so that the patient can resume ordinary daily activities without constant awareness of the presence of the EPG and treatment system. This aspect can be of particular importance in treatment of urge-frequency, overactive bladder and erectile dysfunction, where a patient's awareness of the device could interfere with the patient's experience of symptoms associated with these conditions.

In one aspect, the invention allows for improved assessment of efficacy during trial periods by providing a trial system having improved patient comfort so that patients can more easily recognize the benefits and effectiveness of treatment. In another aspect, the trial system provides a better indication of effectiveness of treatment by utilizing the same implanted neurostimulation lead to deliver the therapy in the permanent system as was used to deliver the therapy in the trial system and further reduces the trauma associated with converting the trial system to the permanent system. In another aspect, the portions of the EPG delivering the therapy are substantially the same as the IPG in the permanent system such that the effects in permanent treatment should be more consistent with those seen in the trial system.

In certain embodiments, the invention provides an EPG patch worn on a skin of the patient so as to improve patient comfort. Optionally, the EPG used in Stage 1 may be smaller than the IPG used in the corresponding Stage 2 so that the EPG can easily be supported by and sealed against contamination by an adherent patch that covers the EPG. In one aspect, the EPG is a modified version of the implantable IPG used in Stage 2. The IPG may be modified by removal of one or more components, such as removal of a remote charging coil with a smaller battery and associated components. In addition, the EPG may use a thinner, lighter housing than the IPG, since the EPG is not required to last for many years, such as the IPG would be. The EPG therefore, may be configured to be disposable. These aspects allow the EPG to be supported within a patch worn on a skin of the patient at a convenient location, such as on the abdomen or side of the patient, as desired.

FIG. 1 illustrates an example trial neurostimulation system 100 having an EPG patch 10. As shown, the neurostimulation system is adapted to stimulate a ventral sacral nerve root. The neurostimulation system 100 includes an implantable pulse generator (IPG) implanted in a lower back region, from which a neurostimulation lead 20 extends through a foramen of the sacrum to electrodes (not shown) disposed near the sacral ventral root. The neurostimulation lead 20 further includes an anchor 10 disposed on a dorsal side of the sacrum. It is appreciated, however, that the anchor may be disposed on a ventral side of the sacrum as well, or within the foramen itself. In one aspect, the EPG 40 is disposable and discarded after the trial is complete. Typically, the trial may last anywhere from 4 days to 8 weeks. Typically, an initial assessment may be obtained after 4-7 days and, if needed, effectiveness of treatment may be examined after a few weeks, typically about 4 weeks. In one aspect, the EPG 40 of the EPG patch 10 is of a substantially similar design as the IPG that would be implanted if the trial proves successful, expect one or more components are removed to allow the EPG to be smaller in size and/or differing materials are used since the device may be intended for one time use.

Figure 2:
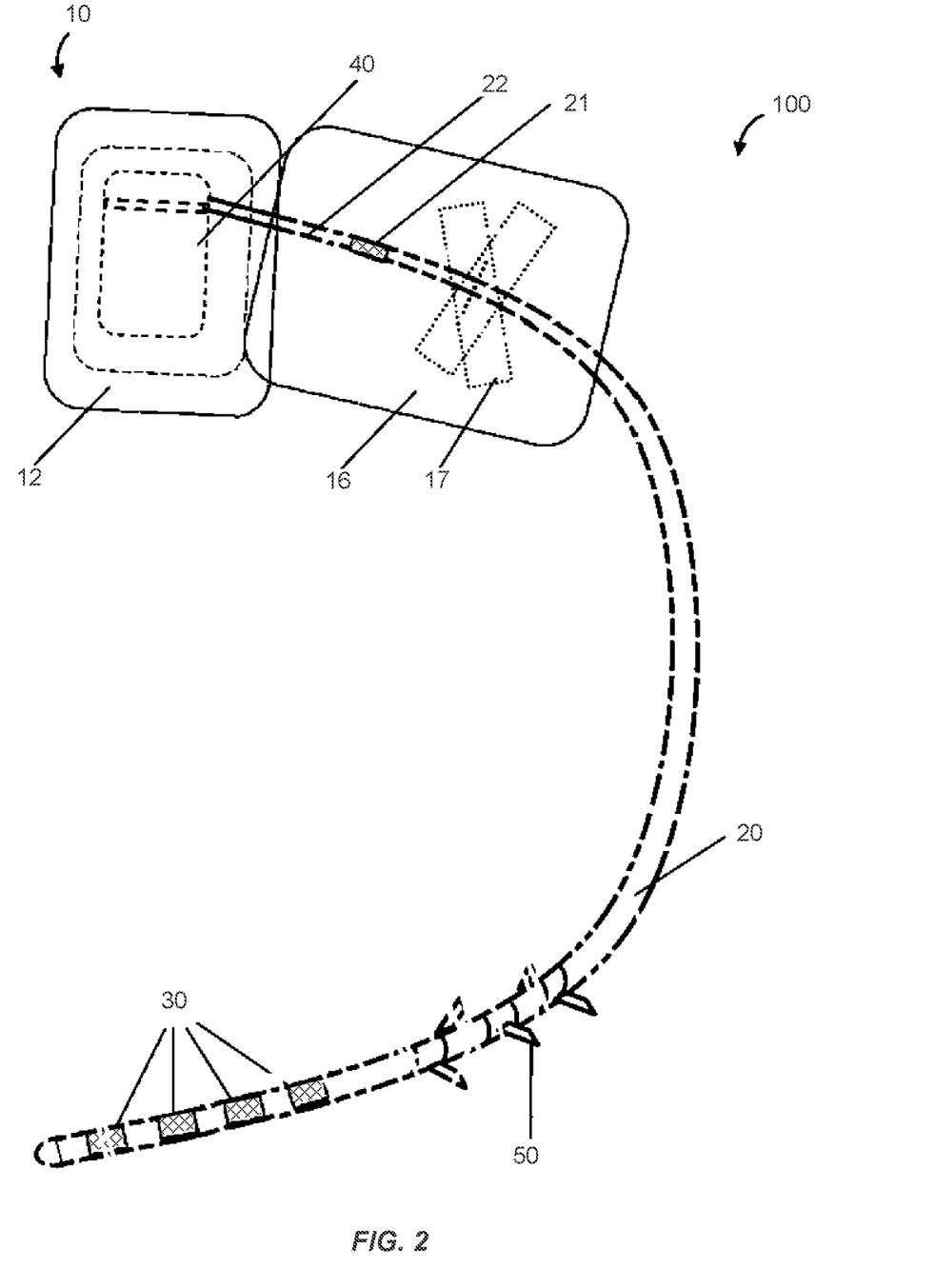
FIG. 2 is an overview of the neurostimulation system of FIG. 1.

FIG. 2 illustrates a neurostimulation system 100, similar to that in FIG. 1, in more detail. As can be seen, the neurostimulation lead 20 includes a plurality of neurostimulation electrodes 30 at a distal end of the lead and an anchor 50 having a plurality of tines disposed just proximal of the electrodes 30. Typically, the anchor is disposed near and proximal of the plurality of electrodes so as to provide anchoring of the lead relatively close to the electrodes. The EPG 40 is supported within an adherent patch 12 when attached to a skin of the patient. In one aspect, the EPG 40 used in the trial period is smaller than the corresponding IPG that would be implanted in a permanent system. This is made possible by removal of components that may not be necessary during a trial period or for an external device, for example the wireless charging coils and associated components. The EPG 40 may utilize a battery thereby allowing the device to be smaller and lighter so as to allow the EPG to be supported by an adherent patch and worn by a patient with minimal discomfort.

In one aspect, additional adherent patches 16 may be used to cover and seal the percutaneous incision in the skin of the patient through which the percutaneous portion of the neurostimulation lead is inserted. The lead may be secured at the percutaneous incision with surgical tape 17 and further secured and sealed with an adherent patch covering the lead and percutaneous incision. In this manner, the percutaneous incision can be sealed and protected from contamination or infection and its position maintained by the additional adherent patches 16. This configuration reduces the likelihood of infection and prevents movement of the lead, both internal and external, such that the patient's awareness of the patch and lead is minimized, thereby allowing the patient to resume relatively normal daily activities.

In another aspect, since the EPG patch may be worn in a different location, such as on the abdomen, than the IPG would be implanted, to allow the IPG to use the same percutaneous portion of the neurostimulation lead 20, the system may use a lead extension 22 coupled with the lead 20 by an external connector 21. The lead extension 22 may be hardwired into the EPG so as to eliminate potential disconnection and allow the connection to be sealed or encapsulated within the adherent patch so as to be water resistant or water proof. This allows the patient to perform routine daily activities, such as showering without removing the device. The length of lead 20 may be a suitable length for the permanently implanted system, while the length of extension 22 allows the lead to EPG patch to be positioned in a location that provide improved comfort and minimized interference with daily activities.

Figure 3:
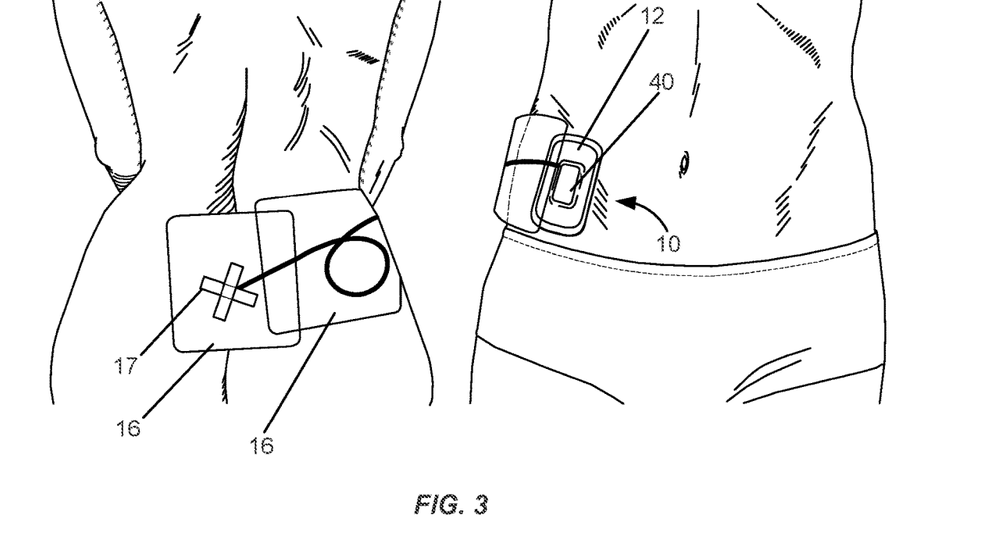
FIG. 3 is an alternative configuration of a trial neurostimulation system, in accordance with aspects of the invention.

FIG. 3 illustrates an alternate configuration in which the lead is sufficiently long to allow the EPG patch 10 to be adhered to the patient's abdomen. This configuration is advantageous as such placement allows the patient more mobility and freedom to resume daily activities and does not interfere with sitting or sleeping. Excess lead can be secured by an additional adherent patch 16, as shown by the center patch in FIG. 3. In one aspect, the lead is hardwired to the EPG, while in another the lead is removable connected to the EPG through a port or aperture in the top surface of the flexible patch 12. In one aspect, the EPG patch is disposable such that the lead can be disconnected and used in a permanently implanted system without removing the distal end of the lead from the target location. In another aspect, the entire system can be disposable and replaced with a lead and IPG.

In one aspect, the EPG unit may be wirelessly controlled by a patient remote in a similar or identical manner as the IPG of a permanently implanted system would be. The physician or patient may alter treatment provided by the EPG through use of a portable clinician unit and the treatments delivered are recorded on a memory of the device for use in determining a treatment suitable for use in a permanently implanted system.

Figure 4:
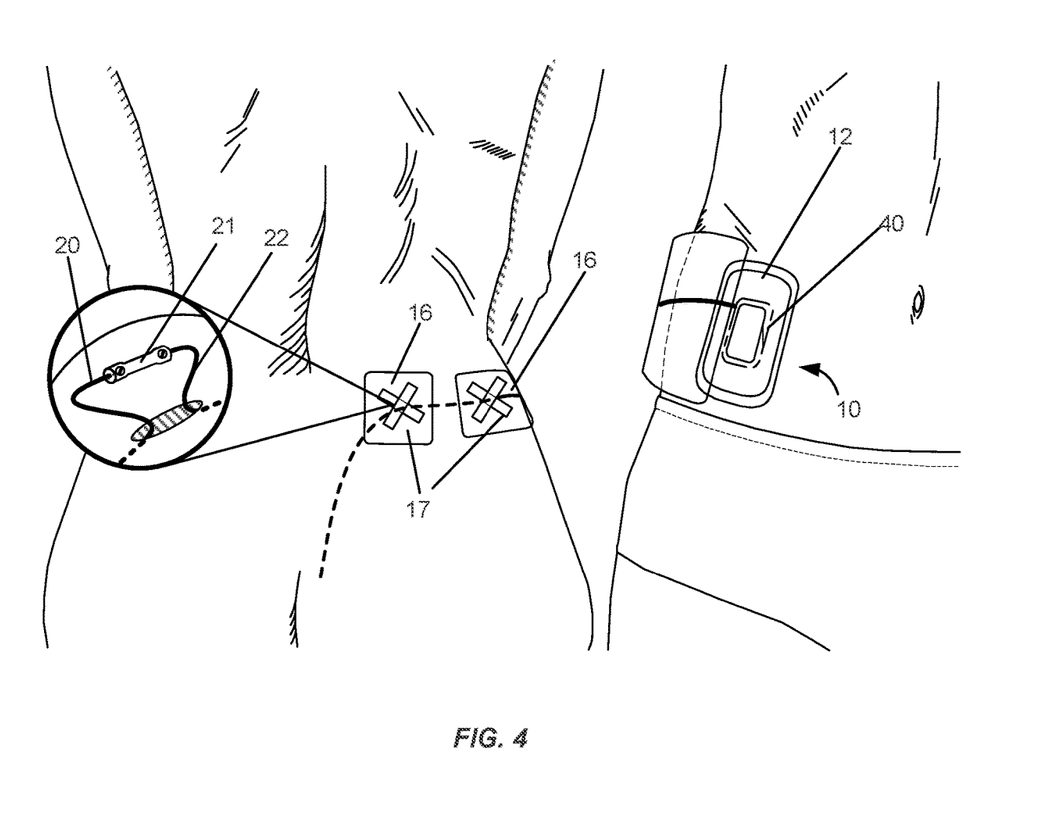
FIG. 4 is yet another alternative configuration of a trial neurostimulation system, in accordance with aspects of the invention.

FIG. 4 illustrates an alternate configuration in which the lead 20 is connected to a lead extension 21 through a connector 21. This allows the lead to be extended so that the EPG patch can be placed on the abdomen. This also allows the lead 20 of a length suitable for implantation in a permanent system to be used. This approach may utilize two percutaneous incisions, the connector 21 provided in the first incision and the lead extensions 12 extending through the second percutaneous incision, there being a short tunneling distance (about 10 cm) therebetween. This approach minimized movement of the implanted lead 20 during conversion of the trial system to a permanently implanted system. During conversion, the lead extension 22 can be removed along with the connector 21 and the implanted lead 20 attached to an IPG that is placed permanently implanted in a location at or near the site of the first percutaneous incision. In one aspect, the connector 21 may include a connector similar in design to the connector on the IPG. This allows the proximal end of the lead 20 to be coupled to the lead extension 22 through the connector 21 and easily detached and coupled to the IPG during conversion to a permanently implanted system.

Figure 5:
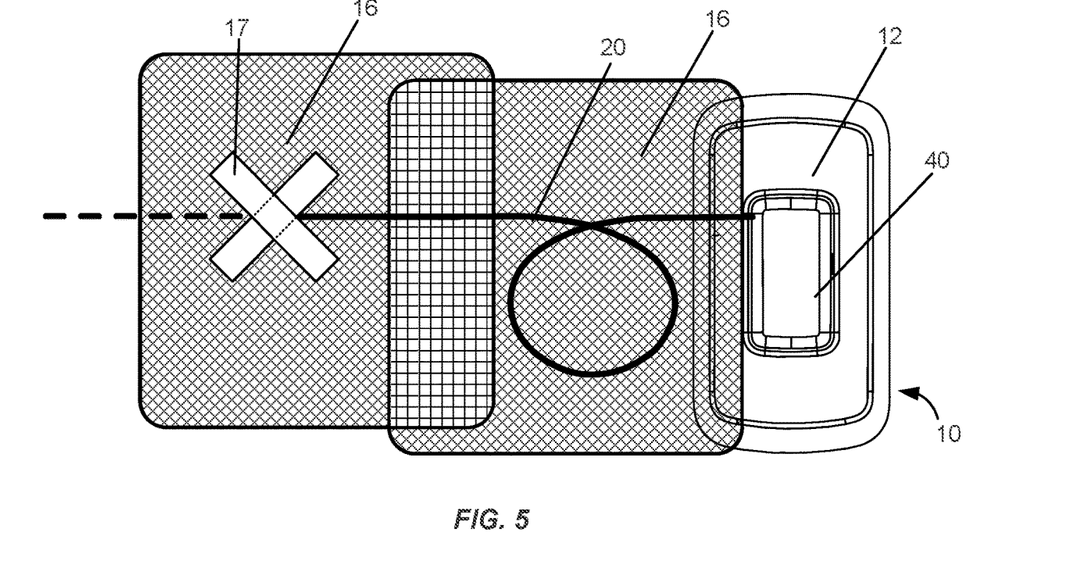
FIG. 5 is a detail of the neurostimulation system in FIG. 3.

FIG. 5 illustrates a detailed view of an EPG patch adhered to the skin of the patient, an additional adherent patch 16 disposed over the percutaneous incision through the lead extends into the patient and another additional patch 16 covering a loop of excess lead, the patch overlapping the first additional patch and the edge of the EPG patch 10. This configuration is advantageous as it substantially covers and seals the EPG and the lead from contamination and prevents accidental disconnection or migration of the lead by the patient, and streamlines the external portions of the system so as to improve patient comfort and allow a patient's subjective experience to more closely match what the patient would experience in a permanently implanted system.

Figure 6:
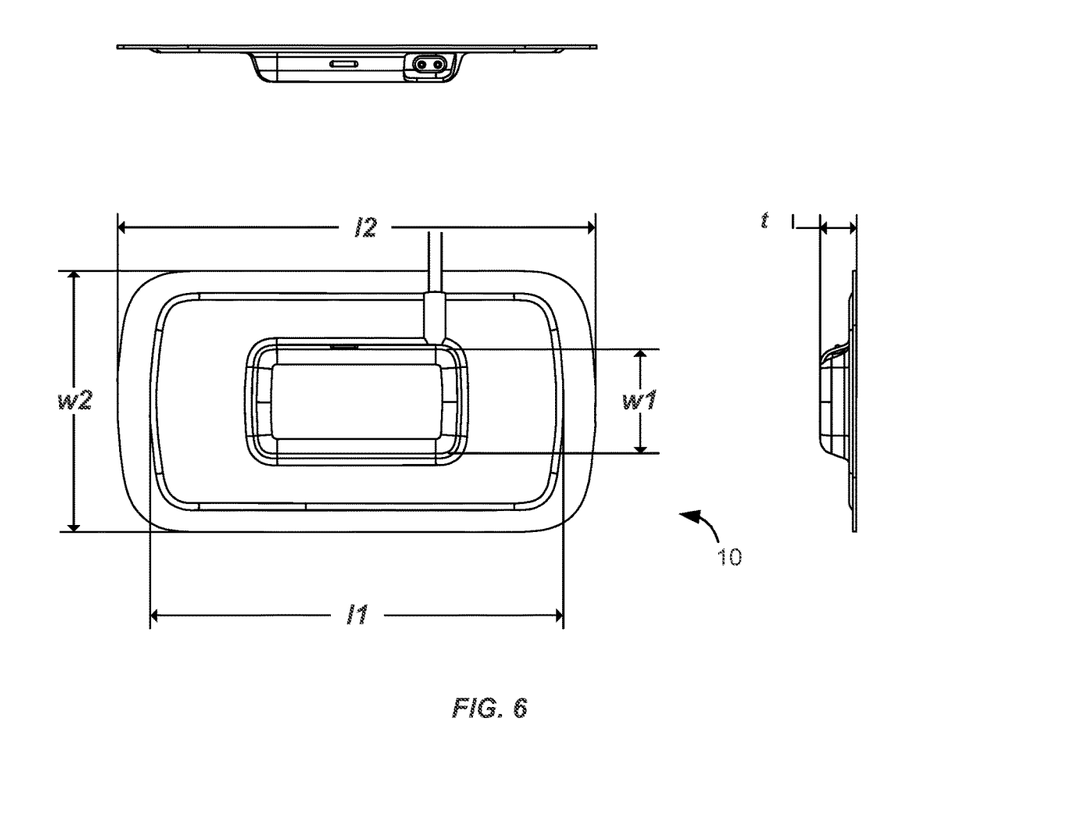
FIG. 6 is an overhead and side views of an example EPG patch, in accordance with aspect of the invention.

FIG. 6 illustrates an overhead view and side views of the EPG patch 10. In one aspect, the EPG is smaller than the IPG in the corresponding fully implantable permanent system. In certain embodiments, the outside width (w2) of the adherent patch 12 is between 2 and 5 inches, preferably about 2.5 inches, while the outside length (l2) of the patch 12 is between 3 and 6 inches, preferably about 4 inches; the width of the EPG (w1) is between 0.5 and 2 inches, preferably about 1 inch, while the length (l1) is between 1 and 3 inches, preferably about 2 inches; and the thickness (t) of the entire EPG patch 10 is less than 1 inches, preferably 0.8 inches or less. This design is considerably smaller than EPGs in conventional systems and thus interferes less with the daily activities of the patient during the trial period.

Figure 7A:
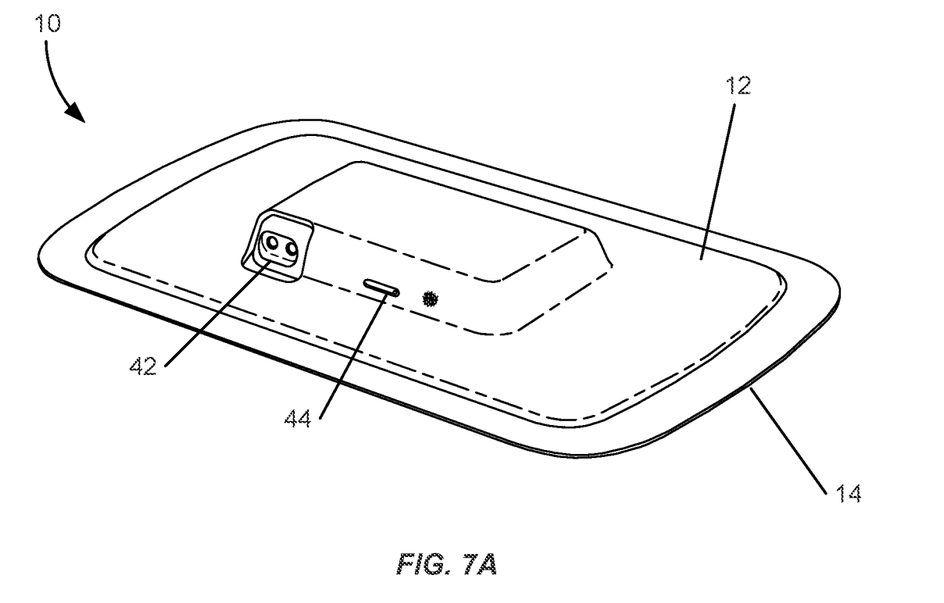
FIGS. 7A-7B illustrate an example EPG patch, in accordance with aspects of the invention.
Figure 7B:
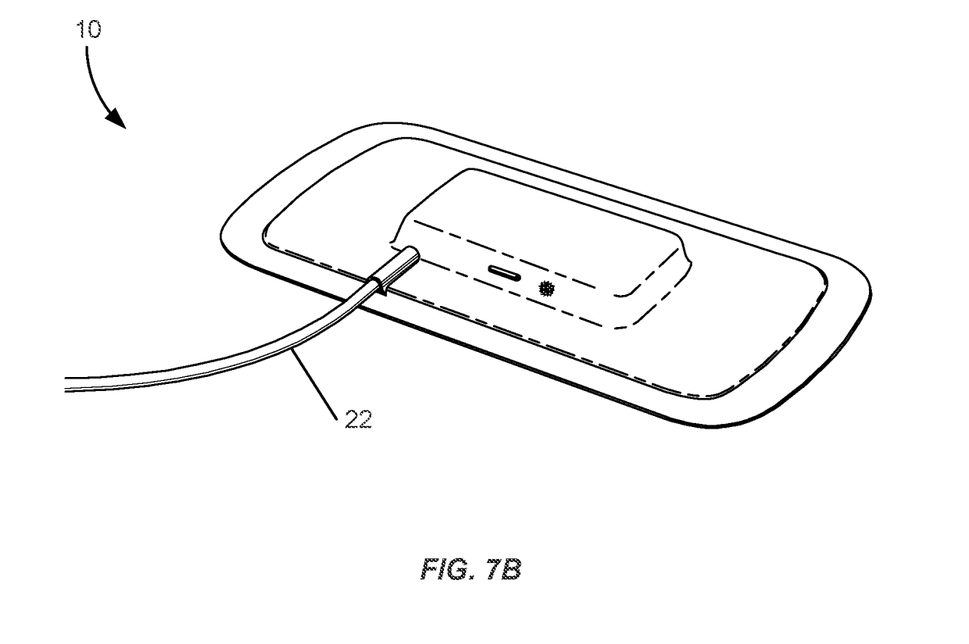

FIGS. 7A-7B illustrate perspective views of two example EPG patches 10. In FIG. 7A, the top surface of the flexible laminated patch 12 provides access to a connection port 42 of the EPG encased inside the patch. The patch may further include an "on/off" button 44 with a molded tactile detail to allow the patient to turn the EPG on and off through the outside surface of the adherent patch 12. The laminated surface of the patch 12 may also be partly transmissive to light such that an LED "on" indicator can be visible through the patch (the glow of the LED light can be seen to the right of the on/off button 44). The underside of the patch 14 is covered with a skin-compatible adhesive. The adhesive surface may be configured with any adhesive or adherent material suitable for continuous adhesion to a patient for the direction of the trial period. For example, a breathable strip having skin-compatible adhesive would allow the patch 12 to remain attached to the patient continuously for over a week, typically two weeks to four weeks, or even longer. In FIG. 7B, the EPG of the EPG patch is hardwired to the lead extension 22. This allows the entire lead extension 22 and EPG to be sealed, thereby improving the water resistance of the system. The advantages associated with embodiments of the EPG patch 10 described above include: disposability; increased patient mobility, including the ability to shower; improved patient comfort; lower infection of risk; and less tunneling through tissues required. These aspects increase the likelihood of trial period success and that patients will convert from the trial system to a permanently implanted system.

Figure 7C:
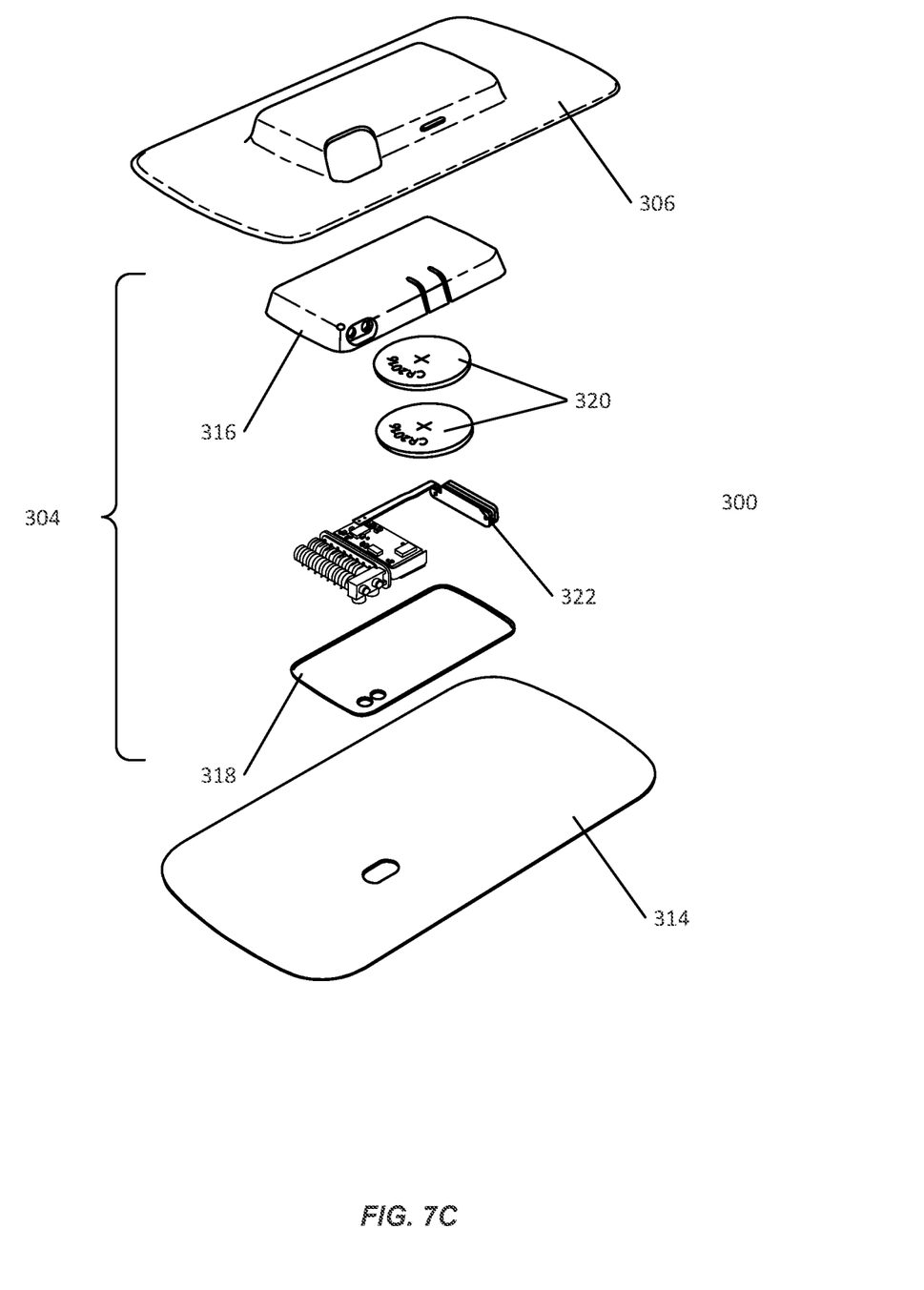
FIG. 7C is an exploded view illustration of an example EPG patch, in accordance with aspects of the invention.

FIG. 7C is an exploded view illustration of an example EPG patch 300. As illustrated, the EPG patch 300 can include a top surface of the patch 306 and a bottom surface of the patch 314 which can be bonded together to encase an EPG 304. Either or both of the top surface of the patch 306 and the bottom surface of the patch 314 can be replaceable and removable, such that both parts are removably bound to each other. The bottom surface of the patch 314 can further include a peel-off liner. The EPG 304 can be constructed of a thin plastic housing forming a shell, having a EPG shell top 316 and an EPG shell bottom 318. Within the shell of the EPG 304 one or more primary cells 320 can be contained, which individually or in combination can provide sufficient power for operation of the EPG 304 for about 14 days of use.

Further, the EPG 304 can include internal circuitry 322 for generating pulses and other functionality.

Figure 8:
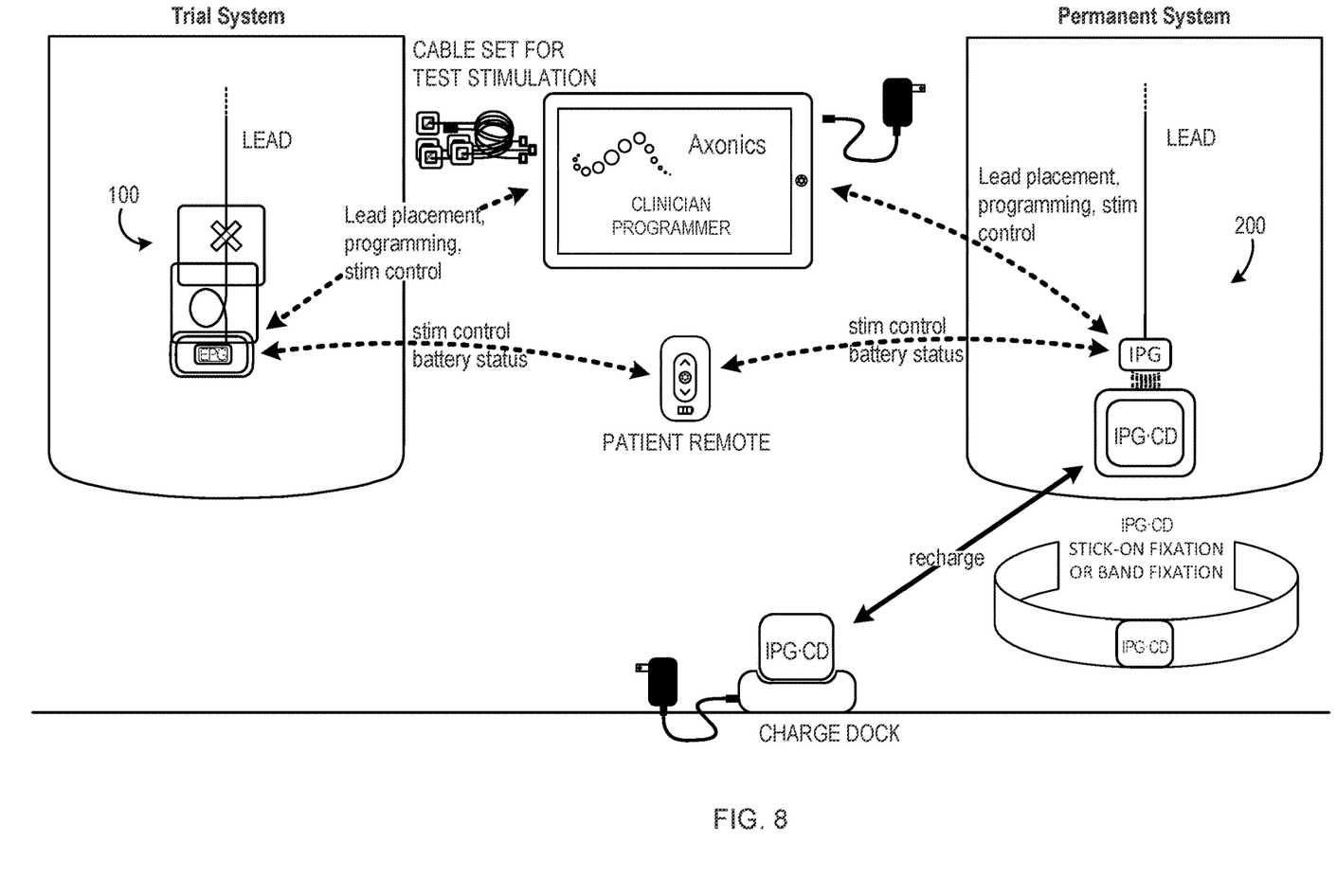
FIG. 8 schematically illustrates a use of a trial neurostimulation system utilizing an EPG patch, in accordance with aspect of the invention.

FIG. 8 illustrates a schematic of a trial system 100, in accordance with aspect of the invention, and a permanent system 200. As can be seen, each of the trial and permanent system are compatible for use with a wireless clinician programmer and a patient remote. The clinician programmer can be used in lead placement, programming and stimulation control in each of the trial and permanent systems. In addition, each allows the patient to control stimulation or monitor battery status with the patient remote. This configuration is advantageous as it allows for an almost seamless transition between the trial system and the permanent system. From the patient's viewpoint, the systems will operate in the same manner and be controlled in the same manner, such that the patient's subjective experience in using the trial system more closely matches what would be experienced in using the permanently implanted system. Thus, this configuration reduces any uncertainties the patient may have as to how the system will operate and be controlled such that the patient will be more likely to convert a trial system to a permanent system.

Figure 9:
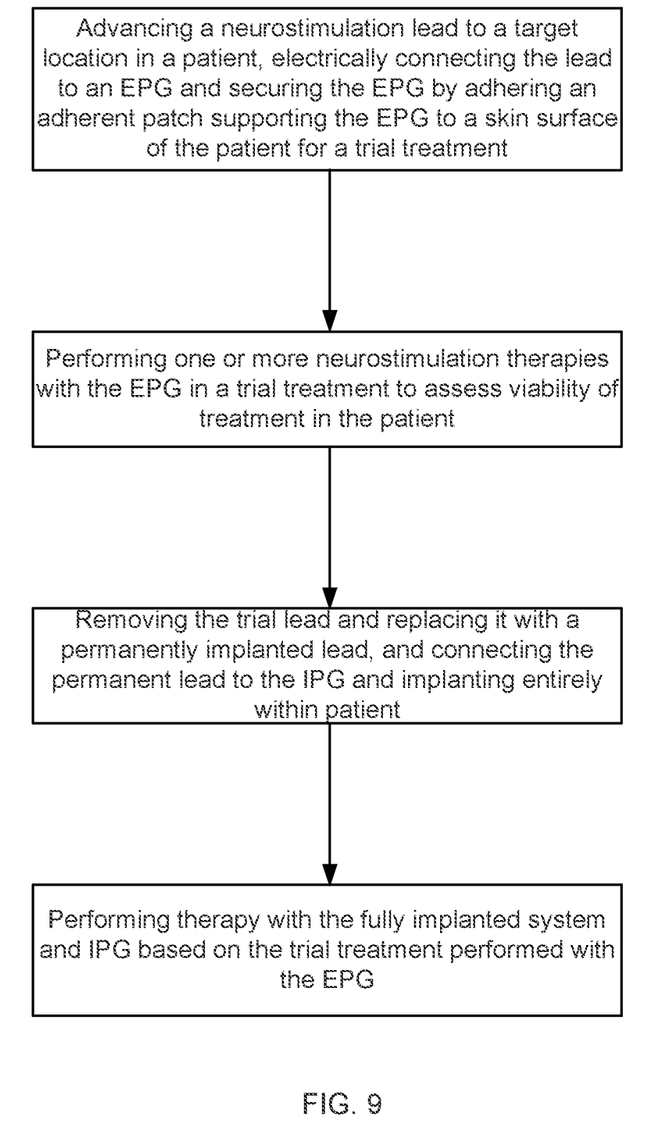
FIGS. 9-10 illustrate methods of performing a trial neurostimulation therapy in accordance with aspects of the invention.
Figure 10:
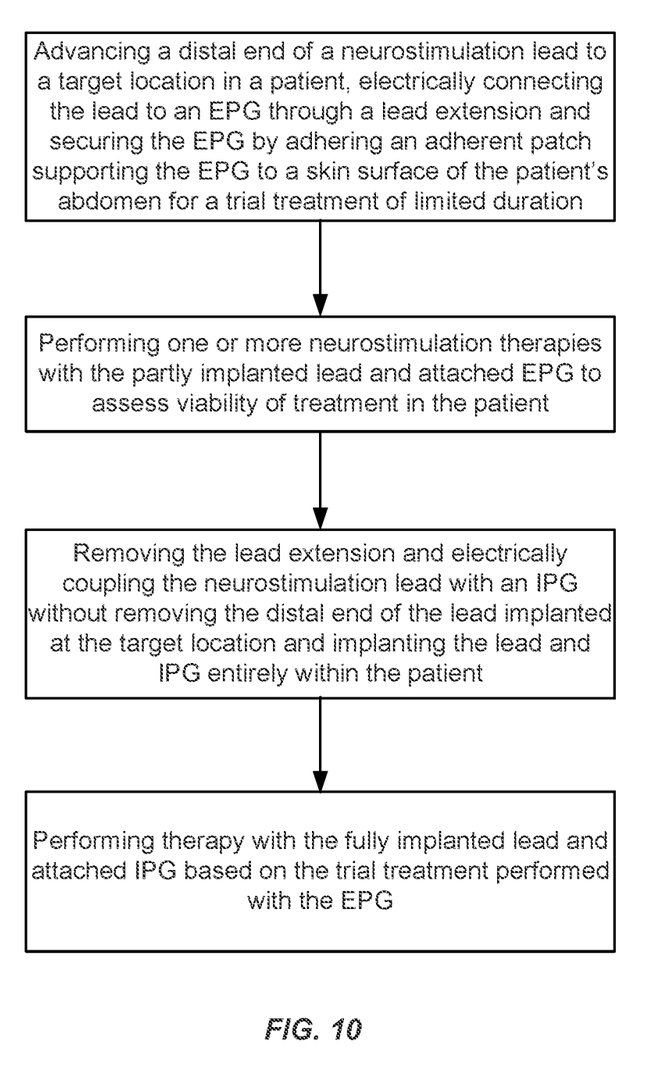

FIGS. 9-10 illustrate methods of treatment that may use an EPG patch in accordance with aspect of the invention. The method of FIG. 9 includes steps of: advancing a neurostimulation lead to a target location in a patient, electrically connecting the lead to an EPG and securing the EPG by adhering an adherent patch supporting the EPG to a skin surface of the patient (or optionally to securing the EPG to a belt worn by the patient) for a trial treatment; performing one or more neurostimulation therapies with the EPG in a trial treatment to assess viability of treatment in the patient; removing the implanted trial lead and replacing it with a permanently implanted lead, and connecting the permanent lead to the IPG and implanting the neurostimulation lead and IPG entirely within the body lead entirely within the patient; and performing therapy with the fully implanted system and IPG based on the trial treatment performed with the EPG.

The method of FIG. 10 includes steps of: advancing a distal end of a neurostimulation lead to a target location in a patient, electrically connecting the lead to an EPG through a lead extension and securing the EPG by adhering an adherent patch supporting the EPG to a skin surface of the patient's skin (or optionally to securing the EPG to a belt worn by the patient) for a trial treatment of limited duration; performing one or more trial neurostimulation therapies with the partly implanted lead and attached EPG to assess viability of treatment in the patient; removing the lead extension and electrically coupling the neurostimulation lead with an IPG without removing the distal end of the lead implanted at the target location and implanting the lead and IPG entirely within the patient; and performing therapy with the fully implanted lead and attached IPG based on the trial treatment performed with the EPG.

In the foregoing specification, the invention is described with reference to specific embodiments thereof, but those skilled in the art will recognize that the invention is not limited thereto. Various features and aspects of the above-described invention can be used individually or jointly. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art.

The invention claimed is:

1. A neurostimulation system comprising:
   an implantable neurostimulation lead having one or more conductors extending from a proximal end of the implantable neurostimulation lead to one or more neurostimulation electrodes disposed at or near a distal end of the implantable neurostimulation lead;
   an external pulse generator electrically coupleable to the implantable neurostimulation lead, the external pulse generator being electrically coupled with the one or more neurostimulation electrodes when electrically coupled with the implantable neurostimulation lead, wherein the external pulse generator is configured to generate a plurality of electrical impulses for delivering a trial neurostimulation treatment to a patient through the one or more neurostimulation electrodes when implanted at a target location;
   wherein the external pulse generator includes a single button, the button being configured to turn on the external pulse generator for delivery of the trial neurostimulation treatment, and wherein a housing of the external pulse generator lacks manual stimulation adjustment controls disposed thereon; and
   an implantable pulse generator adapted to deliver a neurostimulation therapy through the one or more neurostimulation electrodes of the implantable neurostimulation lead based on the trial neurostimulation treatment, wherein the external pulse generator and the implantable pulse generator are configured to wirelessly couple with a patient remote, the patient remote being configured to control stimulation or monitor a battery status of the external pulse generator and the implantable pulse generator in a substantially same manner.

2. The system of claim 1 wherein the implantable pulse generator is configured to operate while implanted for one or more years, while the external pulse generator is configured to be disposable.

3. The system of claim 1 wherein the implantable pulse generator includes a recharging coil and associated components for wireless charging through a skin of the patient while implanted, and the external pulse generator is of a substantially similar configuration of components as the implantable pulse generator but further includes a battery power source and lacks any recharging coil and associated components for wireless charging.

4. The system of claim 3, wherein the battery power source is configured to power the external pulse generator for a duration of a trial period, wherein the duration of the trial period is at least one week.

5. The system of claim 1, wherein the patient remote is configured to facilitate transition between a trial system and a permanent system, wherein the trial system corresponds to the external pulse generator and the permanent system corresponds to the implantable pulse generator.

6. The system of claim 1, further comprising a lead extension electrically coupled to the external pulse generator.

7. The system of claim 6, wherein the lead extension is hardwired with the external pulse generator.

8. The system of claim 6, wherein the lead extension is connected at one end to the proximal end of the implantable neurostimulation lead and coupleable at an opposite end to the external pulse generator or intervening connection.

9. The system of claim 1, further comprising an adherent patch adapted to adhere to a skin of the patient and support the external pulse generator on the skin of the patient for a duration of a trial period.

10. A method of delivering a neurostimulation treatment, the method comprising:
  implanting a distal end of a neurostimulation lead in a target location in a patient, the distal end of the neurostimulation lead having one or more neurostimulation electrodes;
  electrically coupling the neurostimulation lead to an external pulse generator, wherein the external pulse generator includes a single button, the button being configured to turn on the external pulse generator, and wherein a housing of the external pulse generator lacks manual stimulation adjustment controls disposed thereon;
  performing one or more trial neurostimulation treatments with the neurostimulation lead and the external pulse generator during a trial period;
  implanting an implantable pulse generator and connecting to the neurostimulation lead implanted within the patient;
  performing a neurostimulation treatment therapy with the implanted neurostimulation lead and the implantable pulse generator based on the one or more trial neurostimulation treatments performed with the external pulse generator; and
  coupling the implantable pulse generator with a patient remote, wherein the patient remote is configured to control stimulation or monitor a battery status of the implantable pulse generator in a substantially same manner as the external pulse generator.

11. The method of claim 10, wherein performing the one or more trial neurostimulation treatments comprises powering the external pulse generator with a non-rechargeable, non-removable battery power source.

12. The method of claim 10, further comprising:
  powering the external pulse generator with an attached battery, the external pulse generator lacking any recharging coil and components for wireless charging; and
  powering the implantable pulse generator with a power storage unit, the power storage unit being rechargeable through one or more wireless charging coils of the implantable pulse generator.

13. The method of claim 10, wherein performing the one or more trial neurostimulation treatments comprises wirelessly coupling the external pulse generator with a patient remote.

14. The method of claim 13, wherein performing the one or more trial neurostimulation treatments further comprises adjusting stimulation applied by the external pulse generator with an adjustment control of the patient remote.

15. The method of claim 14, wherein performing the one or more trial neurostimulation treatments further comprises powering on the external pulse generator with the button on the external pulse generator and subsequently wirelessly coupling with the patient remote.

16. The method of claim 15, wherein any adjustment of stimulation of the external pulse generator is performed by the patient remote after coupling with the patient remote.

17. The method of claim 14, wherein the patient remote is configured to facilitate transition from a trial system to a permanently implanted system, wherein the trial system corresponds to the external pulse generator and the permanently implanted system corresponds to the implantable pulse generator.

18. The method of claim 10, wherein electrically coupling the neurostimulation lead to the external pulse generator comprises attaching the external pulse generator and lead through a lead extension.

19. The method of claim 18, wherein the lead extension is hardwired to the external pulse generator.

* * * * *